(12) United States Patent
Strobel et al.

(10) Patent No.: US 7,261,716 B2
(45) Date of Patent: Aug. 28, 2007

(54) BIODEGRADABLE INTERFERENCE SCREW AND TOOL FOR ATTACHING A TRANSPLANT TO A BONE

(75) Inventors: Michael Strobel, Straubing (DE); Andreas Weiler, Berlin (DE); Andre Timmermans, Ruurlo (DE)

(73) Assignee: Karl Storz GmbH & Co. KG (DE)

( * ) Notice: Subject to any disclaimer, the term of this patent is extended or adjusted under 35 U.S.C. 154(b) by 164 days.

(21) Appl. No.: 09/745,960

(22) Filed: Dec. 22, 2000

(65) Prior Publication Data

US 2001/0007074 A1    Jul. 5, 2001

(30) Foreign Application Priority Data

Dec. 23, 1999 (EP) .................. 99125925

(51) Int. Cl.
*A61B 17/56* (2006.01)
*A61B 17/04* (2006.01)
*A61F 2/08* (2006.01)
*F16B 23/00* (2006.01)

(52) U.S. Cl. .................. 606/73; 606/60; 606/72; 606/232

(58) Field of Classification Search ................. 606/73, 606/75, 60, 72, 77, 232, 104; 623/13.12, 623/13.14, 13.17, 13.18; 411/418–420, 405

See application file for complete search history.

(56) References Cited

U.S. PATENT DOCUMENTS

| | | | | |
|---|---|---|---|---|
| 3,554,862 A | * | 1/1971 | Hervey et al. ............ 162/158 |
| 3,866,510 A | * | 2/1975 | Eibes et al. ............... 411/418 |
| 3,911,781 A | * | 10/1975 | Bappert .................... 411/418 |
| 5,131,795 A | * | 7/1992 | Kobusch .................... 411/178 |
| 5,364,400 A | * | 11/1994 | Rego et al. ................. 606/72 |
| 5,456,685 A | * | 10/1995 | Huebner ..................... 606/73 |
| 5,470,334 A | * | 11/1995 | Ross et al. .................. 606/72 |
| 5,609,636 A | * | 3/1997 | Kohrs et al. ............. 623/17.16 |
| 5,941,882 A | * | 8/1999 | Jammet et al. ............... 606/73 |
| 6,019,768 A | * | 2/2000 | Wenstrom et al. .......... 606/104 |
| 6,099,530 A | * | 8/2000 | Simonian et al. ............ 606/75 |
| 6,165,203 A | * | 12/2000 | Krebs ........................ 606/232 |
| 6,241,771 B1 | * | 6/2001 | Gresser et al. ........... 623/17.16 |
| 6,379,361 B1 | * | 4/2002 | Beck et al. ................. 606/72 |

(Continued)

FOREIGN PATENT DOCUMENTS

DE    3804749    2/1988

(Continued)

OTHER PUBLICATIONS

A. Weiler, A.C. Stahelin, R.F.G. Hoffmann, N.P. Sudkamp; Biodegradierbare Interferenzschruauben in der Kreuzbandchirurgie,; dated Dec. 14, 1998; 9 pages.

*Primary Examiner*—Justine R. Yu
*Assistant Examiner*—Adam Brandt
(74) *Attorney, Agent, or Firm*—St. Onge Steward Johnston & Reens LLC (57) ABSTRACT

A biodegradable interference screw for directly affixing a transplant to a bone, the interference screw being provided with at least one longitudinal groove designed to co-act with a tool for insertion of and if necessary, removal of the interference screw from an opening provided in the bone to receive both the transplant and the interference screw.

20 Claims, 6 Drawing Sheets

U.S. PATENT DOCUMENTS

| | | | |
|---|---|---|---|
| 6,402,757 B1 * | 6/2002 | Moore et al. | 606/80 |
| 6,454,772 B1 * | 9/2002 | Jackson | 606/73 |
| 6,589,245 B1 * | 7/2003 | Weiler et al. | 606/73 |
| 6,629,977 B1 * | 10/2003 | Wolf | 606/73 |
| 6,863,671 B1 * | 3/2005 | Strobel et al. | 606/73 |
| 2006/0253119 A1 * | 11/2006 | Berberich et al. | 606/72 |

FOREIGN PATENT DOCUMENTS

| | | |
|---|---|---|
| DE | G 9006908 | 6/1990 |
| DE | 41 31 110 | 9/1991 |
| FR | 92 13105 | 11/1992 |
| JP | 11 70126 | 3/1999 |
| WO | WO93/21848 | 4/1993 |
| WO | WO96/25104 | 2/1996 |
| WO | WO99/44533 A1 * | 9/1999 |

* cited by examiner

BIODEGRADABLE INTERFERENCE SCREW AND TOOL FOR ATTACHING A TRANSPLANT TO A BONE

BACKGROUND OF THE INVENTION

The invention relates to a screw for medical purposes having a screw body with a head portion and a following shaft portion having an outer threading. The screw is provided with a recess on which a tool can be applied for turning the screw. The invention further relates to a tool for driving such a screw.

Such screws are disclosed in OP-Journal 14 (1998,) pages 278-284 "Biodegradierbare Interferenzschrauben in der Kreuzbandchirurgie", A. Weiler et al., Georg Thieme Verlag, Stuttgart, N.Y.

Interference screws have the purpose of anchoring a tendon or a ligament transplant to a bone. A channel is drilled into the bone in which the transplant is to be inserted. The screw is driven into the intermediate space between the transplant and an inner wall of the channel, so that the transplant is then clamped between the screw and the inner channel wall.

Considerable forces arise in such a tendon or a ligament, for example the cruciate ligaments in a knee joint, so that the clamping force must be correspondingly high to ensure a reliable anchoring. The screw is therefore provided with an outer threading which penetrates into the bone material at the inner side of the bore channel. At the same time, the outer threading engages with the transplant to be anchored.

Other fields of application for screws exist for the interconnection of materials. A central opening is provided in the head for rotating the screw, in which a tool can be placed, for example a corresponding screw driver. Since considerable forces are exerted on the screw, especially at the last few turns before the final seating, this opening is provided not only in the head region, for driving means engaging at the head, but extends centrally and axially far into the shaft region. The forces from the tool are then not only transferred to the head but are distributed over larger regions of the screw body. This is done especially to prevent the head from being sheared off from the rest of the screw body, especially for the last turns before the final seating.

It is known to produce such screws of metals, in particular titanium, however screws of biodegradable material have also found wider application. It has been found that biodegradable screws made of suitable materials have the same high initial anchoring strength as metal screws. However, considerable difficulties arise when driving the screws.

If the central opening has the form of a hexagon, into which a tool in the form of a hex head socket wrench is inserted, the danger exists, especially for biodegradable materials, that the hexagonal contour is destroyed and the tool then turns without frictional connection. For this reason, attempts have been made to select other cross-sectional forms of the central opening, which allow a greater surface contact with the tool. For example, FIG. 3 of the above-mentioned publication in the OP-Journal shows such cross-sections, in the form of a cross or a turbine. The tendency is to produce a relatively large and branched central opening, so that only a relatively thin wall remains for the screw body.

This has the disadvantage, especially for small and thin screws with very thin walls that the twist resistance is no longer sufficient to withstand the high forces applied when driving in the screw. This tendency of increasingly larger central openings also leads to the screw body having a relatively large central hollow volume. This has a disadvantage, especially for biodegradable screws that when the thin wall of the biodegradable body is biologically degraded after a relatively short time, a large hollow space results. With this, a sufficient clamping force is no longer present to hold the tendon or ligament transplant in place.

It is therefore an object of the present invention to overcome the above problems and to provide a screw which can reliably receive high driving forces even for smaller and thinner constructions, without being deformed or damaged.

SUMMARY OF THE INVENTION

According to the present invention, a screw is provided in which the opening or recess is provided in the form of at least one axial groove which is cut into the outer side of the screw body, said at least one groove extending along said head portion and an entire length of said shaft portion.

It is also now possible to produce extremely small and thin screws of biodegradable material, because the central massive body is sufficient to withstand the high forces when driving in the screw without causing a twisting or destruction of the screw. In addition, the stability is maintained even for slow biological degradation, so that the remaining hollow space cannot collapse.

Furthermore, a considerable advantage with biodegradable material for the screws is that no hollow body with a large inner cavity is present, which could expose the surrounding mantle when the hollow body is decomposed and could lead to loosening of the tendon transplant. Rather, the central massive screw body can slowly degrade and new biological material can grow from the outside, so that the central compact body is replaced by this biological material with time. Thus, it is excluded that relatively large hollow spaces could become exposed after a certain decomposition time of a thin wall, which would lead to an instability of the anchoring.

The provision of axial grooves on the outer side of the screw body is simple to accomplish from a manufacturing standpoint, namely both for screws of metal and biodegradable materials.

The provision of a groove extending along said head portion and an entire length of said shaft portion has the advantage that the forces applied by a tool inserted into the groove acts on the screw body in a manner distributed over the entire length of the screw body. This contributes further to the stability of the body, especially for very small and thin interference screws.

In a further embodiment of the present invention, the cutting depth of the at least one axial groove is provided such that a drive element of the tool lies within the groove and does not extend or only negligibly extends beyond the outer peripheral contour of the screw. The feature has the considerable advantage that a tool applied to the screw does not extend beyond the outer contour, so that substantially only the outer threading of the screw comes into contact with the tendon transplant and the inner wall of the boring in the bone and not the tool. The particular advantage is that small cavities result about the circumference of the screw body when withdrawing the tool, which were previously filled with the tool when driving in the screw. After withdrawing the tool, bone or transplant material can move back into these cavities for solid anchoring.

A screw can be securely applied also when the tool extends beyond the circumference of the screw only slightly or only at a few locations, i.e. when only one or two axial grooves are present, a screw can be tightly seated with such a tool. Due to the fact that the porous bone material and also the material of the tendon or ligament has a certain flexibility, the tool can be removed after placement of the screw, and material can move back into the so produced free spaces and additionally provide for the solid anchoring of the screw.

In a further embodiment of the present invention, at least one recess is provided on the end face of the head portion, in which a corresponding projection on the tool can be inserted. The feature has the advantage that this recess in the head acts as a placement means or centering aid for the tool. This leads to an exact alignment of the tool on the screw.

In a further embodiment of the present invention, the recess is configured as a channel passing through the screw body. This is of advantage particularly for relatively large screws, that material can grow into the inner hollow space during biological degradation of the body surrounding this hollow space via the channel. A simultaneous growth of material into the screw body parallel with its biological degradation is possible in particular for configurations in which the outer side of the body has additional openings or holes which join into the central channel.

In a further embodiment, several axial grooves are provided to be distributed about the outer circumference of the screw body. The feature has the advantage that the forces act not only through a single axial groove, but simultaneously over several axial grooves arranged uniformly about the circumference of the screw body. With very thin screw bodies, the extremely high torques are then uniformly distributed over the body, which excludes the danger of deformation or shearing caused by momentary peaks in the force.

In a further embodiment, one to five axial grooves are provided, more particularly three grooves. The number of grooves allow an optimal force distribution for thin screws and a correspondingly stable tool, i.e. within the range of conventional sizes for such screws.

In a further embodiment, the axial groove is open axially at the end face of the head portion. The feature has the advantage that the tool can be pushed onto the screw axially and especially after applying the screw can be axially removed therefrom via this opening. This advantageously leads to a smooth withdrawal of the tool after driving in the screw, especially in conjunction with the above embodiment where the tool does not extend beyond the periphery of the screw. This is possible without impairing the material surrounding the screw, i.e. bone material and the tendon or ligament.

In a further embodiment, the axial groove, in particular in the head portion, is cross-connected over the circumference with at least one bridge. The feature has the advantage that the bridge prevents the tool, after having been placed on the screw, from being displaced to the side or in radial direction from the screw. This is of particular advantage when only one single axial groove is present. Since no outer threading is normally cut into such screws in the head region, a higher material diameter is present in the region of the head, so that it is possible to enclose the head with an outer peripheral bridge even with the axial groove being cut therein.

Such a bridge can also be formed by the winding of the threading projecting from the outer surface of the screw body. In some types of screws, relatively large windings are present, so that a sufficiently solid bridge of material remains.

According to the present invention, a tool is also provided for driving a screw having at least one drive element which is insertable into the at least one axial groove. A tool is provided to be exactly adapted to the construction of the respective screw or the configuration of its axial groove, i.e. a tool adapted to the number, the geometry and the length of the grooves. Thus, an optimal interaction and handling between the tool and the screw is guaranteed. This also contributes to achieving the object of the present invention.

In a further embodiment of the tool, the at least one drive element is configured such that it is insertable from the head side in the longitudinal direction in the corresponding axial groove. The feature has the advantage in handling that the tool can be placed on the screw and vice versa by holding the tool in one hand, attaching the screw thereon and then placing it at the corresponding location where the screw is to be applied. The tolerances between the width of the axial groove and the width of the corresponding drive element for the groove can be selected so that the screw sits firmly on the tool. This simplifies the work of the operator, i.e. he need not worry that the screw will fall off the tool.

In the embodiment where the axial groove, especially in the head portion is cross-connected by at least one bridge element, the advantage results, as mentioned above, that the bridge prevents a displacement of the screw to the side or a tilting, especially in conjunction with a screw having only one single groove.

In a further embodiment, at least one projection extends from the distal side of the tool, which can pass into a recess on the end face of the head portion of the screw. The feature has the considerable advantage that this projection acts as a centering aid when placing the screw on the tool. If the screw has only one axial groove, the projection of the tool extending into the recess on the screw head provides an additional safety feature that the tool does not rotate out of the screw when turning the tool.

In a further embodiment, when several drive elements are present, the drive elements are connected to one another by peripheral bridges. The feature has the advantage that a radial spreading of long and thin drive elements is avoided. Breakage points can be provided so that the bridges break off from the drive elements when withdrawing the tool and remain on the screw. In this manner, the tool can be simply withdrawn from the tightened screw.

It will be understood that the above-mentioned features and those to be described below are applicable not only in the given combinations, but also in other combinations or taken alone without departing from the scope of the present invention.

BRIEF DESCRIPTION OF THE DRAWINGS

The invention will be discussed in more detail below in conjunction with selected embodiments and the appended drawings.

DETAILED DESCRIPTION OF PREFERRED EMBODIMENTS

Figure 1:
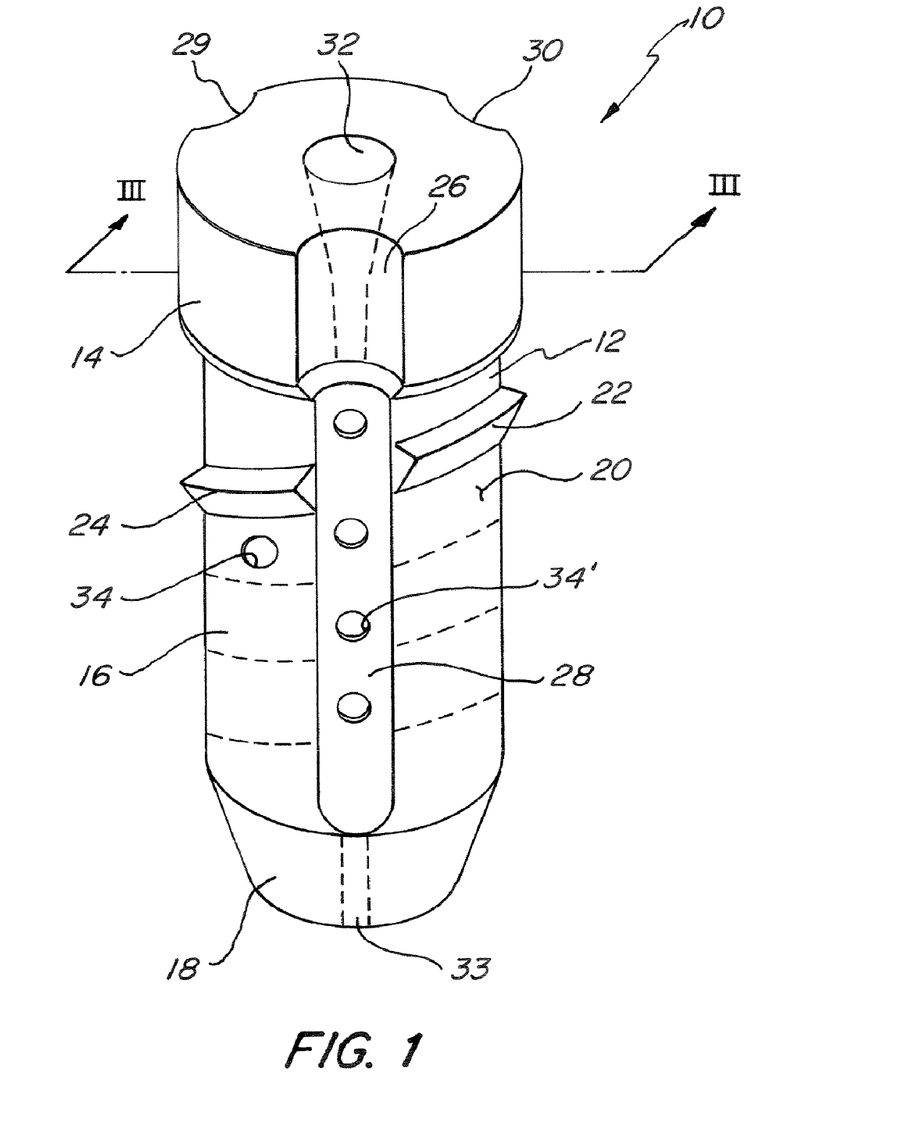
FIG. 1 shows a perspective side view of a screw according to the present invention with three axial grooves uniformly distributed about the circumference.

A screw shown in FIG. 1 is indicated with the numeral 10 and is configured as an interference screw. The interference screw 10 comprises an interference screw body 12 having a head portion 14 and a following shaft portion 16, which ends in a tapered penetration end 18. The interference screw 10 can be made of metal, for example titanium, however is most preferably made of biodegradable material. Examples of biodegradable materials are polycaprolactone, poly(L-lactide), polyglycol, poly(D,L-lactide), poly(D,L-lactide-co-glycol), poly(D,L-lactide-cocaptrolactone), polydioxanone, copolyoxalates and polycarbonates, for example, polyglycol-co-trimethylenecarbonate and poly(glutamine-co-leucine).

The interference screw 10 is provided with an outer threading 22 in the region of the shaft portion 16 at its outer surface 20. Only one winding 24 of the threading 22 is shown in FIG. 1, the other windings only being indicated with dashed lines. A first recess 26 in the form of an axially disposed groove 28 is provided on the outer side 20. The depth of the axial groove 28 is such that it is cut into both the head portion 14 and the shaft portion 16 from the outside. Since the threading 22 is provided in the shaft region 16, the axial groove 28 also cuts through the threading 22 as shown by the winding 24.

Figure 3:
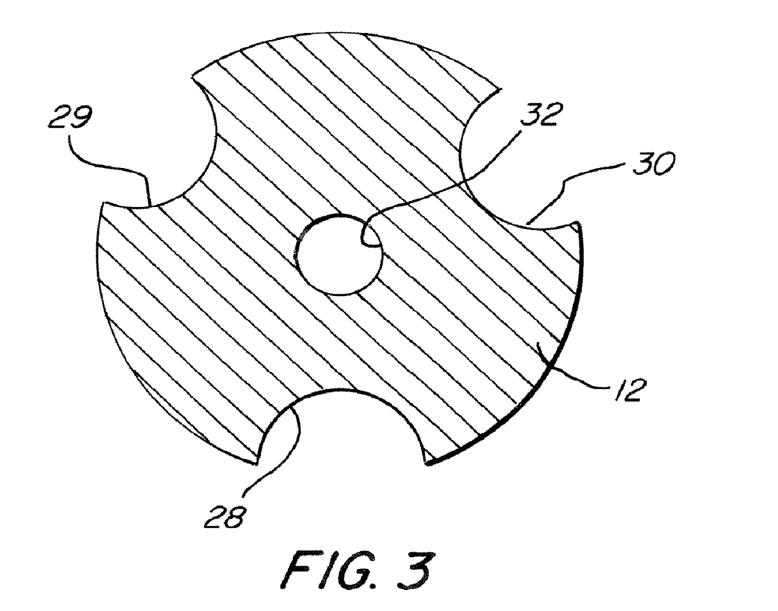
FIG. 3 shows a cross-section along the line III-III in FIG. 1.

The depth and the form is best seen in the cross-section of FIG. 3, i.e. the groove 28 has the form of a section of a circle in cross-section. The groove 28 thus extends from the end face of the head portion 14 over the entire shaft portion 16 to the tapered penetration end 18. The groove 28 is open at the end face of the head portion 14.

Two further grooves 29, 30 are provided to be symmetric to the groove 28 about the periphery, which are formed to be identical to the groove 28. The angular spacing of the three grooves 28, 29 and 26 with respect to one another is therefore 120 degrees.

A recess 32 is provided at the center of the head portion 16, which in the present embodiment runs from a conically tapered section into a thin central channel 33, which extends to the penetration end 18 and communicates to the outside there.

Figure 2:
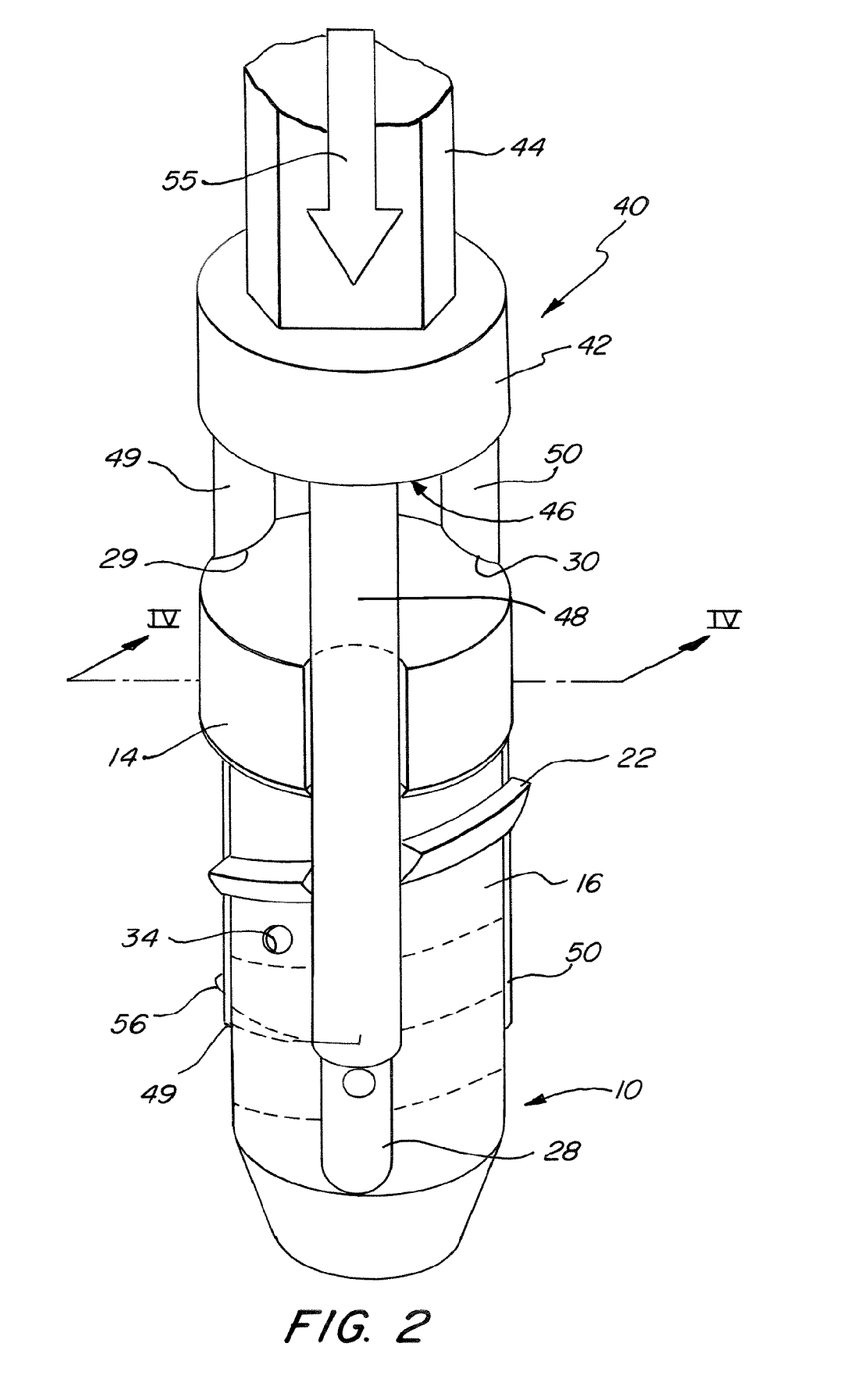
FIG. 2 shows an illustration corresponding to FIG. 1 with a tool placed on the screw.

In addition, numerous axially directed bores or holes 34, 34' are provided in the screw body 12 which communicate with the central channel 33. The central recess 32 serves as a centering aid for a tool 40, as shown in FIG. 2. A projection 54 is provided on the tool 40 (see in particular the cross-sectional view of FIG. 4) which is formed as a pin and can be inserted into the recess 32.

The purpose of the openings 34, 34' communicating with the central channel 33 is that when the interference screw is made of biodegradable material, the biological material then can grow inwardly through these openings into the interior space. An intertwined structure with biologically grown material then results, whose degradable portion biologically decomposes with time. Since the growth of the biological material is normally faster than the biological degradation, an intertwined and networked composite is formed between the biological material surrounding the interference screw and its interior space, namely at a time before the biologically degradable material of the screw has decomposed.

This offers the possibility, especially for revisions, to apply a further boring in the region of the interference screw 10, since sufficient biological material has already formed there into which a new tendon transplant can be placed.

Figure 4:
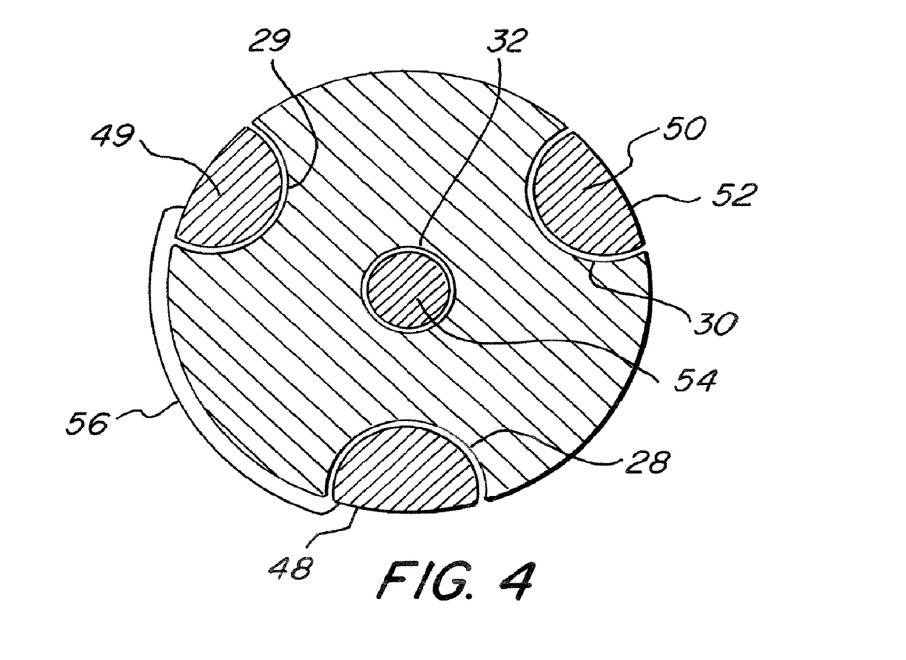
FIG. 4 shows a cross-section along the line IV-IV in FIG. 2.

As can be taken from the illustration of FIG. 2 and the cross-sectional illustration of FIG. 4, a tool 40 for applying the interference screw 10 has a head 42 from which a grip 44 extends in the proximal direction.

Three drive elements 48, 49, 50 extend from the underside 46 of the head 42. The peripheral arrangement, configuration and length of the three drive elements 48, 49, 50 is such that they can pass into the three grooves 28, 29, 30.

The cross-section 52 of the rod-like drive element, for example the element 50 shown in FIG. 4, is such that it precisely fills out the clearance inner space of the corresponding groove 30. This holds in the same manner for the other drive elements 48, 49. It then follows that the drive elements 48, 49, 50 when inserted into the grooves 28, 29, 30 do not extend beyond the periphery of the screw body 12.

With respect to handling, the tool 40 as shown in FIG. 2 is slipped onto the interference screw 10 from the proximal end over the head portion 14, namely in an alignment such that the three drive elements 48, 49, 50 are inserted into the drive grooves 28, 29, 30. The central projection 54 on the underside of the head 42 of the tool 40 (hidden by the drive element 48 in FIG. 2) is somewhat shorter than the drive elements 48, 49, 50. It enters the recess 32 at about the position shown in FIG. 2 from the proximal side of the head of the interference screw 10 and provides a sufficient centering effect. The tool 40 is pushed axially forward as indicated by an arrow 45 in FIG. 2 until the underside 46 of the tool 40 lies on the end face of the head portion 14.

As can be seen from FIG. 2, the drive elements 48, 49, 50 cover numerous holes 34', so that it is ensured when turning the interference screw that the holes do not produce further resistance or that undesired material enters the screw already when being screwed in.

A relatively large-surface frictional engagement is present between the tool 40 and the interference screw 10 due to the axial length of the three drive elements 48, 49, 50 and the form-fit in the grooves 28, 29, 30, so that considerable torques can be reliably transmitted even for relatively small and thin interference screws. Individual or even all of the drive elements can be interconnected at their circumference to avoid a radial spreading. This is indicated in FIGS. 2 and 4 with a bridge 56 which cross-connects the drive elements 48, 49, 50 in circumferential direction at the distal end region. The bridge 56 is configured such that it does not hinder the application or the withdrawal of the tool 40. Such a bridge can also be formed by one or more winding 24 of the threading 22, for example when the winding 24 shown in FIG. 1 continues transversely over the axial groove 28.

After applying the interference screw, the tool 40 can be simply withdrawn in opposite direction of the arrow 55 shown in FIG. 2, as will be described in the following in conjunction with a further embodiment.

Figure 5:
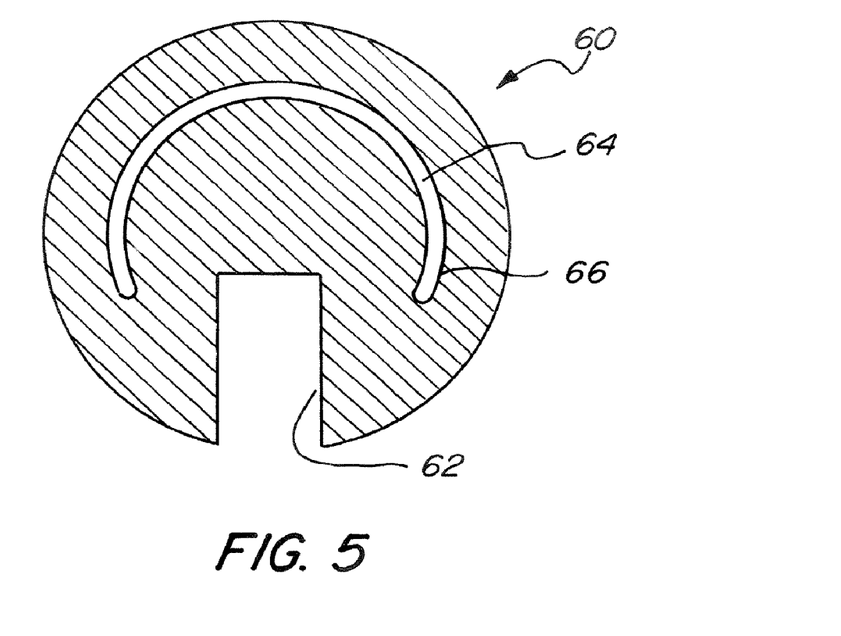
FIG. 5 shows an illustration comparable to the cross-section in FIG. 3 of a further embodiment of a screw.

A further embodiment of the interference screw 60 is shown in FIG. 5, by which only one axial groove 62 has been cut into its outer surface. A recess 64 in the form of a partial circumferential slot 66 serves as a placement element or a centering aide for a correspondingly configured tool.

The depth and the width of the groove 62 is somewhat greater than the three grooves in the embodiment of the interference 10. The deeper cut however leaves a compact and solid body at the center of the interference screw 16, such that no twisting or shearing of the interference screw 60 takes place even with considerably high torques. The axial groove 62 in this case also extends through the head portion and a further region of the shaft portion of the interference screw 60.

Figure 6:
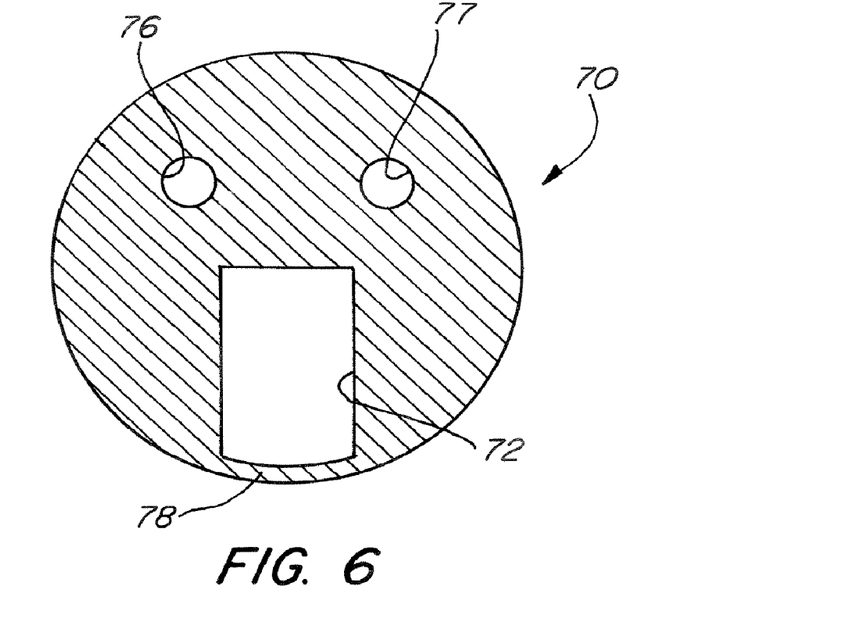
FIG. 6 shows a cross-section corresponding to FIG. 3 or FIG. 5 of a further embodiment of a screw.

FIG. 6 shows a further embodiment of an interference screw 70 which also has only one axial groove 72, as above with the interference screw 60. Two blind holes 76, 77 are provided in the head portion of interference screw 70 as a centering aid for the corresponding tool 80.

Figure 7:
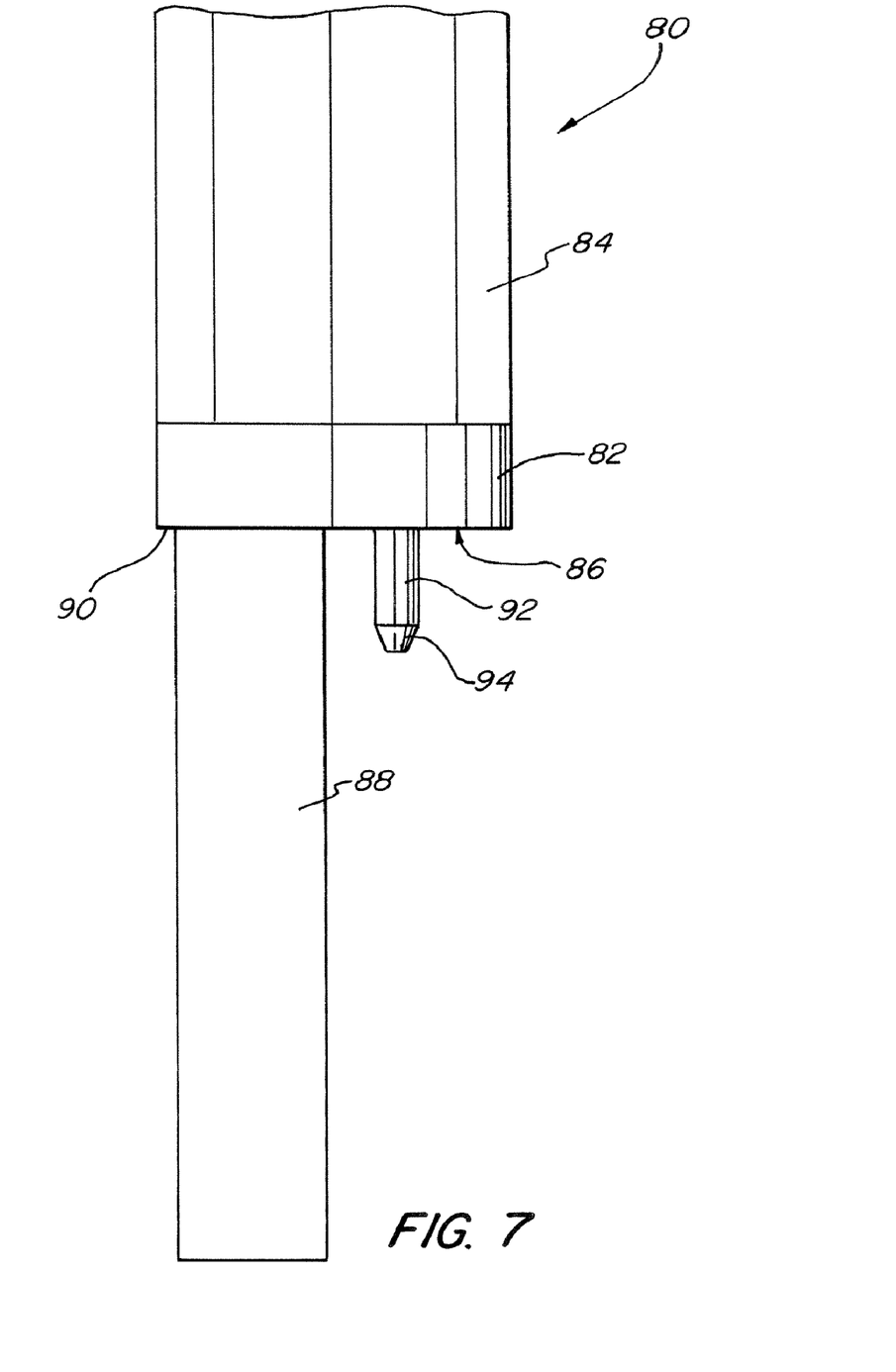
FIG. 7 shows a side view of a tool for engagement with the screw illustrated in FIG. 6.

From the cross-section of FIG. 6, it can be seen that the axial groove 72 is closed at the circumference in the region of the head portion by an outer bridge 78. The corresponding tool 80 shown in FIG. 7 has a head 82 from which a grip 84 extends for handling from the proximal end. A drive element 88 extends from the underside 86 of the head 82, which has an approximately rectangular cross-section and whose cross-sectional contour corresponds to the cross-section of the groove 72. The drive element 88 is slightly displaced inwardly at the outer periphery, so that a step 90 results, where the displacement corresponds to the radial width of the bridge 78. Projections 92 extend from the underside 86 in the form of two pins 94, 94', which can be inserted in the corresponding blind holes 76, 77 of the interference screws 70 when the tool 80 is slid over the interference screw 70 from the proximal end.

Figure 8:
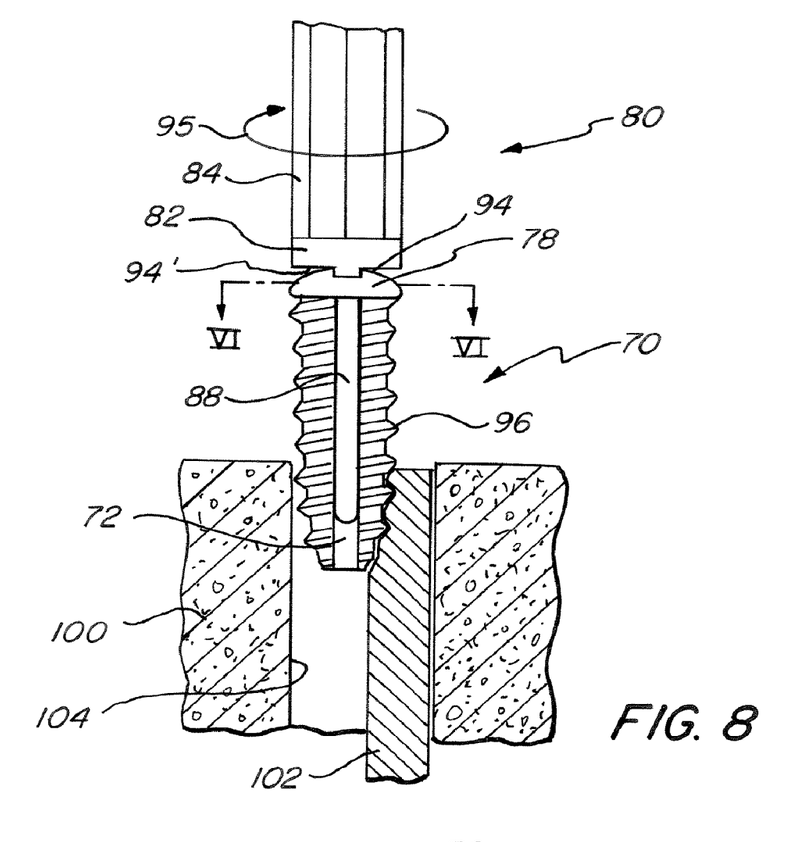
FIG. 8 shows a partial cross-section of a screw of the embodiment of FIG. 6, where a tool corresponding to the illustration of FIG. 7 is placed on the screw to begin the fixing of a tendon transplant.

This situation is illustrated in FIG. 8. As can be seen, the tool 80 is placed on the interference screw 70 such that the drive element 88 is inserted from the top into the axial groove 72 and is protected from being displaced to the side by the bridge 78. When the tool is completely mounted, its underside 86 lies against top side of the head of the interference screw 70. As can be seen from FIG. 8, the groove 72 has been cut into the entire axial length of the interference screw 70, i.e. it also cuts through the outer threading 96.

Figure 9:
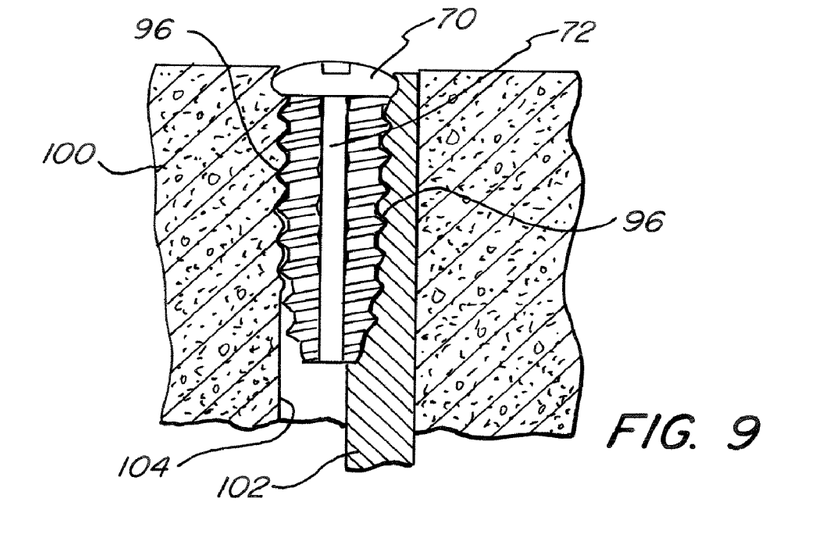
FIG. 9 shows the screw illustrated in FIG. 8 after being completely applied to anchor the tendon transplant.

The procedure of anchoring with the screw is illustrated in the sequence of FIGS. 8 and 9. An opening in the form of a bore channel 104 is made in the bone 100 into which the tendon transplant 102 is placed. The diameter of the bore channel 104 is selected such that the tendon 102 or an end thereof can be inserted.

When replacing a cruciate ligament, corresponding borings are made both in the femur and in the tibia and the ligament is anchored at both locations as is shown for example in FIG. 1 of the above-mentioned article in the OP-Journal.

After inserting a tendon or ligament transplant 102, the interference screw 70 with the mounted tool 80 is placed such that its penetration end is located between the inner wall of the bore channel 104 and the outer end of the transplant 102. This setting and inserting is more easily accomplished through the tapering in the region of the penetration end.

By rotating the tool 80, as indicated by the arrow 95 in FIG. 8, the interference screw is applied. The outer threading 96 grinds into the material of the bone 100 and also penetrates into the relatively flexible material of the transplant 102 without injuring or destroying the same. The transplant is clamped or pressed into the remaining intermediate space between the interference screw 70 and the bore channel 104.

The turning of the screw by the tool 80 is not hindered because the drive element 88 of the tool 80 does not extend beyond the outer contour of the interference screw 70. After complete application of the interference screw 70, the tool 80 can be simply withdrawn axially without changing the position or the seating of the interference screw 70 in any way. This situation is shown in FIG. 9, i.e. the interference screw 70 is completely tightened down and the tool 80 has been removed.

It is now possible even with extremely small and thin interference screws to transmit the considerable forces for turning the interference screw by the tool disposed in the axial grooves, so that interference screws can be applied at the desired locations without impairing their stability or structure.

The invention claimed is:

1. An interference screw for anchoring a transplant to a bone comprising:
   a screw body made of a biodegradable material, said screw body including a head and a shaft and at least one axially extending groove substantially the length of said screw body and cut into an outer side of said screw body;
   said screw head having a recess located therein;
   a tool for inserting the screw into an opening in the bone, said tool including a drive element for insertion into said at least one axially extending groove;
   said tool having a protrusion corresponding to said recess in the screw head for centering said tool with respect to said screw body during insertion;
   said screw body adapted to contact the transplant positioned between said screw body and a side of the opening in the bone to anchor said transplant to said bone.

2. The interference screw according to claim 1 wherein said at least one drive element extends substantially the length of said at least one axially extending groove.

3. The interference screw according to claim 1 wherein a depth of the at least one axially extending groove is such that the at least one drive element of said tool lies within the at least one axially extending groove and does not extend beyond an outer periphery of said screw body.

4. The interference screw according to claim 1 wherein a depth of the at least one axially extending groove is such that the at least one drive element of said tool is housed within the at least one axially extending groove without extending radially beyond a threading of said shaft.

5. The interference screw according to claim 1 wherein said recess is configured as a channel completely passing through said screw body.

6. The interference screw according to claim 1 wherein the at least one axially extending groove is open axially at said screw head.

7. The interference screw according to claim 1 wherein a bridge is provided for bridging the at least one axially extending groove in a circumferential direction.

8. The interference screw according to claim 7 wherein said bridge is provided in said screw body.

9. The interference screw according to claim 1 wherein a bridge is provided for bridging the at least one axially extending groove in an circumferential direction of said screw body, said bridge is formed by an outer threading of said shaft.

10. The interference screw according to claim 1 wherein the transplant is selected from the group consisting of: a tendon, a ligament, and combinations thereof.

11. An interference screw for anchoring a transplant to a bone comprising:
    a screw body made of a biodegradable material, said screw body including a head and a shaft and at least three axially extending grooves;

a tool for inserting the screw into an opening in the bone, said tool including at least three drive elements for insertion into said at least three axially extending grooves;

said screw body adapted to contact the transplant positioned between said screw body and a side of the opening in the bone to anchor said transplant to said bone;

said at least three axially extending grooves cut into an outer side of said screw body.

12. The interference screw according to claim 11 wherein said at least three axially extending grooves are substantially the length of said screw body.

13. The interference screw according to claim 11 wherein said at least three drive elements extend substantially the length of said at least three axially extending grooves.

14. The interference screw according to claim 11 wherein a depth of the at least three axially extending grooves is such that the at least three drive elements of said tool lies within the at least three axially extending grooves and does not extend beyond an outer periphery of said screw body.

15. The interference screw according to claim 11 wherein a depth of the at least three axially extending grooves is such that the at least three drive elements of said tool is housed within the at least three axially extending grooves without extending radially beyond a threading of said shaft.

16. The interference screw according to claim 11 wherein the at least three axially extending grooves are open axially at said screw head.

17. The interference screw according to claim 11 wherein a bridge is provided for bridging at least one of the at least three axially extending grooves in a circumferential direction.

18. The interference screw according to claim 17 wherein said bridge is provided in said screw body.

19. The interference screw according to claim 11 wherein a bridge is provided for bridging the at least one of the at least three axially extending grooves in an circumferential direction of said screw body, said bridge is formed by an outer threading of said shaft.

20. The interference screw according to claim 11 wherein the transplant is selected from the group consisting of: a tendon, a ligament, and combinations thereof.

\* \* \* \* \*